United States Patent
Markwell et al.

(10) Patent No.: US 6,989,447 B2
(45) Date of Patent: Jan. 24, 2006

(54) COMPOUNDS

(75) Inventors: Roger Edward Markwell, Great Dunmow (GB); Neil David Pearson, Knebworth (GB)

(73) Assignee: SmithKline Beecham p.l.c., Brentford (GB)

( * ) Notice: Subject to any disclaimer, the term of this patent is extended or adjusted under 35 U.S.C. 154(b) by 6 days.

(21) Appl. No.: 10/720,788

(22) Filed: Nov. 24, 2003

(65) Prior Publication Data

US 2004/0116452 A1 Jun. 17, 2004

Related U.S. Application Data

(63) Continuation of application No. 10/031,768, filed as application No. PCT/EP00/06940 on Jul. 17, 2000, now abandoned.

(30) Foreign Application Priority Data

Jul. 23, 1999 (GB) ............................................. 9917406

(51) Int. Cl.
C07D 215/16 (2006.01)
C07D 237/26 (2006.01)
A61K 31/47 (2006.01)

(52) U.S. Cl. ...................... 546/152; 514/248; 514/259; 514/300; 514/312; 544/235; 544/237; 544/284; 546/122; 546/123; 546/153

(58) Field of Classification Search ................. 546/152, 546/153, 122, 123; 514/312, 248, 259, 300; 544/235, 237, 284
See application file for complete search history.

(56) References Cited

U.S. PATENT DOCUMENTS

| | | | |
|---|---|---|---|
| 5,310,743 A | 5/1994 | Schilling et al. | |
| 5,541,195 A | 7/1996 | Schilling et al. | |
| 5,646,144 A | 7/1997 | Schilling et al. | |
| 5,710,158 A * | 1/1998 | Myers et al. | 514/266.2 |
| 6,602,882 B1 | 8/2003 | Davies et al. | |

FOREIGN PATENT DOCUMENTS

| | | |
|---|---|---|
| BE | 706646 | 5/1968 |
| DE | 2315148 A | 10/1973 |
| EP | 0031753 | 7/1981 |
| EP | 0042781 | 12/1981 |
| EP | 0053964 | 6/1982 |
| EP | 0 238 868 A2 | 2/1987 |
| EP | 0 823 429 A1 | 2/1988 |
| EP | 0 304 493 A1 | 3/1988 |
| EP | 0 673 927 A1 | 6/1988 |
| EP | 0296560 | 12/1988 |
| EP | 0 374 095 A2 | 12/1989 |
| EP | 0449186 | 10/1991 |
| EP | 0 532 456 A1 | 8/1992 |
| EP | 0 541 486 A1 | 10/1992 |
| EP | 0572963 | 12/1993 |
| EP | 0 532 456 B1 | 3/1995 |
| EP | 0742207 | 11/1996 |
| EP | 0 913 393 B1 | 10/1998 |
| EP | 0 913 393 A2 | 5/1999 |
| EP | 0 926 139 A1 | 6/1999 |
| EP | 0030044 | 1/2001 |
| EP | 0 673 927 B1 | 9/2001 |
| GB | 1 496 371 | 12/1977 |
| JP | 2169569 | 6/1990 |
| NL | 7908030 | 6/1981 |
| WO | WO 91/03243 | 3/1991 |
| WO | WO 92/02502 | 2/1992 |
| WO | WO 92/17475 | 10/1992 |
| WO | WO 95/09853 | 4/1995 |
| WO | WO 96/15128 | 5/1996 |
| WO | WO 96/38144 | 12/1996 |
| WO | WO 96/39145 | 12/1996 |
| WO | WO 97/03069 | 1/1997 |
| WO | WO 97/28167 | 8/1997 |
| WO | WO 97/45119 | 12/1997 |
| WO | WO 98/02438 | 1/1998 |
| WO | WO 99/37635 | 7/1999 |
| WO | WO 00/21948 | 4/2000 |
| WO | WO 00/21952 | 4/2000 |
| WO | WO 01/25227 | 4/2001 |

OTHER PUBLICATIONS

Kayirere et al., *Synthesis and Antibacterial Activity of New 4–Alkoxy, 4–Aminoalkyl and 4–Alkylthioquinoline Derivatives*, Eur. J. Med. Chem., vol. 33, pp. 55–63 (1998).
U.S. Appl. No. 09/600,984, filed Jan. 21, 1999, Coates et al.
U.S. Appl. No. 09/807,275, filed Oct. 11, 1999, Hatton et al.
U.S. Appl. No. 10/032,403, filed Dec. 20, 2001, Hatton et al.
U.S. Appl. No. 09/807,341, filed Oct. 11, 1999, Davies et al.
U.S. Appl. No. 10/018,900, filed Jun. 13, 2000, Davies et al.
U.S. Appl. No. 10/013,844, filed Jul. 17, 2000, Davies et al.

\* cited by examiner

*Primary Examiner*—D. Margaret Seaman
(74) *Attorney, Agent, or Firm*—Grace C. Hsu; Mary E. McCarthy; Charles M. Kinzig

(57) ABSTRACT

Aminopiperidine derivatives and pharmaceutically acceptable derivatives thereof useful in methods of treatment of bacterial infections in mammals, particularly in man.

11 Claims, No Drawings

COMPOUNDS

This application is a continuation of U.S. Ser. No. 10/031,768 filed Jul. 17, 2000 now abandoned, which is a 371 of PCT/EP00/06940, filed Jul. 17, 2000.

This invention relates to novel compounds, compositions containing them and their use as antibacterials.

DE2315148A, EP0030044, NL7908030, EP0053964, EP0031753, EP0042781 and BE706646 disclose quinoline compounds having cardiovascular, hypnotic, anticonvulsant, and antimalarial effects.

EP0579263, EP0742207, JP2169569, EP0296560, WO9103243, EP0449186 disclose piperidine compounds as acetylcholinesterase inhibitors and sigma receptor antagonists.

WO9802438 and WO9703069 disclose certain bicyclic heteroaromatic compounds having protein tyrosine kinase and cell proliferation inhibitor activity.

WO9217475, WO9802438, WO9703069 and WO9639145 disclose certain bicyclic heteroaromatic compounds having cholinesterase inhibitor, protein tyrosine kinase inhibitor, cell proliferation inhibitor and human epidermal growth factor receptor type 2 inhibitor activity.

WO99/37635, WO00/21948 and WO00/21952 disclose piperidine derivatives having antibacterial activity.

We have now found a novel group of aminopiperidines which have antibacterial activity.

This invention provides a compound of formula (I) or a pharmaceutically acceptable derivative thereof:

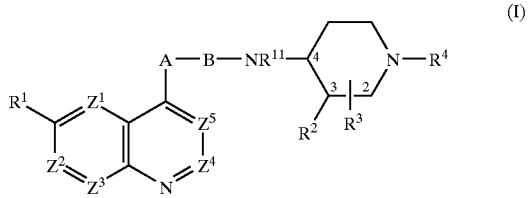

wherein:
one of $Z^1$, $Z^2$, $Z^3$, $Z^4$ and $Z^5$ is N, one is $CR^{1a}$, and the remainder are CH, or one of $Z^1$, $Z^2$, $Z^3$, $Z^4$ and $Z^5$ is $CR^{1a}$, and the remainder are CH;

$R^1$ and $R^{1a}$ are independently hydrogen; hydroxy; $(C_{1-6})$ alkoxy optionally substituted by $(C_{1-6})$alkoxy, amino, piperidyl, guanidino or amidino optionally N-substituted by one or two $(C_{1-6})$alkyl, acyl or $(C_{1-6})$alkylsulphonyl groups. $CONH_2$, hydroxy, thiol, $(C_{1-6})$alkylthio, heterocyclylthio, heterocyclyloxy, arylthio, aryloxy, acyloxy or $(C_{1-6})$alkylsulphonyloxy; $(C_{1-6})$alkoxy-substituted$(C_{1-6})$alkyl; halogen; $(C_{1-6})$alkyl; $(C_{1-6})$ alkylthio; nitro; azido; acyl; acyloxy; acylthio; $(C_{1-6})$ alkylsulphonyl; $(C_{1-6})$alkylsulphoxide; arylsulphonyl; arylsulphoxide or an amino, piperidyl, guanidino or amidino group optionally N-substituted by one or two $(C_{1-6})$ alkyl, acyl or $(C_{1-6})$alkylsulphonyl groups; and
additionally when $Z^5$ is $CR^{1a}$, $R^{1a}$ may be $(C_{1-4})$alkyl-$CO_2H$ or $(C_{1-4})$alkyl-$CONH_2$ in which the $C_{1-4}$ alkyl is substituted by $R^{12}$; $(C_{1-4})$alkyl substituted by amino, cyano or guanidino; aminocarbonyl optionally substituted by hydroxy, $(C_{1-6})$alkyl, hydroxy$(C_{1-6})$alkyl, aminocarbonyl $(C_{1-6})$alkyl, $(C_{2-6})$alkenyl, $(C_{1-6})$alkylsulphonyl, trifluoromethylsulphonyl, $(C_{2-6})$alkenylsulphonyl, $(C_{1-6})$ alkoxycarbonyl, $(C_{1-6})$alkylcarbonyl, $(C_{2-6})$ alkenyloxycarbonyl, $(C_{2-6})$alkenylcarbonyl, or $CH(R^{13})$ $CO_2H$ or $CH(R^{13})CONH_2$ optionally further substituted by $(C_{1-6})$alkyl, hydroxy$(C_{1-6})$alkyl, aminocarbonyl$(C_{1-6})$ alkyl or $(C_{2-6})$alkenyl; hydroxy$(C_{1-6})$alkyl; carboxy; cyano or $(C_{1-6})$alkoxycarbonyl;
wherein $R^{13}$ is a natural α-amino acid side chain, or its enantiomer;
provided that when one of $Z^1$, $Z^2$, $Z^3$, $Z^4$ and $Z^5$ is $CR^{1a}$ and the remainder are CH, then $R^1$ is not hydrogen;
$R^2$ is hydrogen;
$R^3$ is hydrogen; or
$R^3$ is in the 2-, 3- or 4-position and is:
carboxy; $(C_{1-6})$alkoxycarbonyl; aminocarbonyl wherein the amino group is optionally substituted by hydroxy, $(C_{1-6})$ alkyl, hydroxy$(C_{1-6})$alkyl, aminocarbonyl$(C_{1-6})$alkyl, $(C_{2-6})$alkenyl, $(C_{1-6})$akylsulphonyl, trifluoromethylsulphonyl, $(C_{2-6})$alkenylsulphonyl, $(C_{1-6})$ alkoxycarbonyl, $(C_{1-6})$alkylcarbonyl, $(C_{2-6})$ alkenyloxycarbonyl or $(C_{2-6})$alkenylcarbonyl and optionally further substituted by $(C_{1-6})$alkyl, hydroxy$(C_{1-6})$ alkyl, aminocarbonyl$(C_{1-6})$alkyl or $(C_{2-6})$alkenyl; cyano, tetrazolyl; 2-oxo-oxazolidinyl optionally substituted by $R^{10}$; 3-hydroxy-3-cyclobutene-1,2-dione-4-yl; 2,4-thiazolidinedione-5-yl; tetrazol-5-ylaminocarbonyl; 1,2,4-triazol-5-yl optionally substituted by $R^{10}$; or 5-oxo-1,2,4-oxadiazol-3-yl; or $(C_{1-4})$alkyl or ethenyl optionally substituted with any of the substituents listed above for $R^3$ and/or up to 3 groups $R^{12}$ independently selected from: thiol; haloen; $(C_{1-6})$alkylthio; trifluoromethyl; azido; $(C_{1-6})$alkoxycarbonyl; $(C_{1-6})$alkylcarbonyl; $(C_{2-6})$ alkenyloxycarbonyl, $(C_{2-6})$alkenylcarbonyl; hydroxy optionally substituted by $(C_{1-6})$alkyl, $(C_{2-6})$alkenyl, $(C_{1-6})$ alkoxycarbonyl, $(C_{1-6})$alkylcarbonyl, $(C_{2-6})$ alkenyloxycarbonyl, $(C_{2-6})$alkenylcarbonyl or aminocarbonyl wherein the amino group is optionally substituted by $(C_{1-6})$alkyl, $(C_{2-6})$alkenyl, $(C_{1-6})$alkylcarbonyl or $(C_{2-6})$ alkenylcarbonyl; amino optionally mono- or disubstituted by $(C_{1-6})$alkoxycarbonyl, $(C_{1-6})$alkylcarbonyl, $(C_{2-6})$ alkenyloxycarbonyl, $(C_{2-6})$alkenylcarbonyl, $(C_{1-6})$alkyl, $(C_{2-6})$alkenyl, $(C_{1-6})$alkylsulphonyl, $(C_{2-6})$alkenylsulphonyl or aminocarbonyl wherein the amino group is optionally substituted by $(C_{1-6})$alkyl or $(C_{2-6})$alkenyl; aminocarbonyl wherein the amino group is optionally substituted by $(C_{1-6})$ alkyl, hydroxy$(C_{1-6})$alkyl, aminocarbonyl$(C_{1-6})$alkyl, $(C_{2-6})$ alkenyl, $(C_{1-6})$alkoxycarbonyl, $(C_{1-6})$alkylcarbonyl, $(C_{2-6})$ alkenyloxycarbonyl or $(C_{2-6})$alkenylcarbonyl and optionally further substituted by $(C_{1-6})$alkyl, hydroxy$(C_{1-6})$alkyl, aminocarbonyl$(C_{1-6})$alkyl or $(C_{2-6})$alkenyl; oxo; $(C_{1-6})$ alkylsulphonyl; $(C_{2-6})$alkenylsulphonyl; or $(C_{1-6})$ aminosulphonyl wherein the amino group is optionally substituted by $(C_{1-6})$alkyl or $(C_{2-6})$alkenyl;
in addition when $R^3$ is disubstituted with a hydroxy or amino containing substituent and a carboxy containing substituent these may together form a cyclic ester or amide linkage, respectively; or
when $R^3$ is in the 3-position $R^2$ and $R^3$ may together form a divalent residue $=CR^{5'}R^{6'}$ where $R^{5'}$ and $R^{6'}$ are independently selected from hydrogen, $(C_{1-6})$alkyl, $(C_{2-6})$ alkenyl, aryl$(C_{1-6})$alkyl and aryl$(C_{2-6})$alkenyl, any alkyl or alkenyl moiety being optionally substituted by up to three $R^{12}$ groups;
$R^4$ is a group $—CH_2—R^5$ in which $R^5$ is selected from:
$(C_{1-12})$alkyl; hydroxy$(C_{1-12})$alkyl; $(C_{1-12})$alkoxy$(C_{1-12})$ alkyl; $(C_{1-12})$alkanoyloxy$(C_{1-12})$alkyl; $(C_{3-6})$cycloalkyl; hydroxy$(C_{3-6})$cycloalkyl; $(C_{1-12})$alkoxy$(C_{3-6})$cycloalkyl; $(C_{1-12})$alkanoyloxy$(C_{3-6})$cycloalkyl; $(C_{3-6})$cycloalkyl$(C_{1-12})$alkyl; hydroxy-, $(C_{1-12})$alkoxy- or $(C_{1-12})$alkanoyloxy-$(C_{3-6})$cycloalkyl$(C_{1-12})$alkyl; cyano; cyano$(C_{1-12})$alkyl; $(C_{1-12})$alkenyl; $(C_{1-12})$alkynyl; tetrahydrofuryl; mono- or di-$(C_{1-12})$alkylamino$(C_{1-12})$alkyl;

acylamino($C_{1-12}$)alkyl; ($C_{1-12}$)alkyl- or acylaminocarbonyl($C_{1-12}$)alkyl; mono- or di-($C_{1-12}$) alkylamino(hydroxy) ($C_{1-12}$)alkyl; optionally substituted phenyl($C_{1-12}$)alkyl, phenoxy($C_{1-12}$)alkyl or phenyl (hydroxy)($C_{1-12}$)alkyl; optionally substituted diphenyl ($C_{1-12}$)alkyl; optionally substituted phenyl($C_{1-12}$)alkenyl; optionally substituted benzoyl or benzoyl($C_{1-12}$)alkyl; optionally substituted heteroaryl or heteroaryl($C_{1-12}$) alkyl; and optionally substituted heteroaryl or heteroaroyl ($C_{1-12}$)alkyl;

A is $CR^6R^7$ and B is $SO_2$, CO or $CH_2$ wherein:

each of $R^6$ and $R^7$ is independently selected from: hydrogen; ($C_{1-6}$)alkoxy; thiol; ($C_{1-6}$)alkylthio; halo; trifluoromethyl; azido; ($C_{1-6}$)alkyl; ($C_{2-6}$)alkenyl; ($C_{1-6}$)alkoxycarbonyl; ($C_{1-6}$)alkylcarbonyl; ($C_{2-6}$)alkenyloxycarbonyl; ($C_{2-6}$) alkenylcarbonyl; hydroxy, amino or aminocarbonyl optionally substituted as for corresponding substituents in $R^3$; ($C_{1-6}$)alkylsulphonyl; ($C_{2-6}$)alkenylsulphonyl; or ($C_{1-6}$)aminosulphonyl wherein the amino group is optionally substituted by ($C_{1-6}$)alkyl or ($C_{2-6}$)alkenyl;

$R^{10}$ is selected from ($C_{1-4}$)alkyl; ($C_{2-4}$)alkenyl and aryl any of which may be optionally substituted by a group $R^{12}$ as defined above; carboxy; aminocarbonyl wherein the amino group is optionally substituted by hydroxy, ($C_{1-6}$) alkyl, ($C_{2-6}$)alkenyl, ($C_{1-6}$)alkylsulphonyl, trifluoromethylsulphonyl, ($C_{2-6}$)alkenylsulphonyl, ($C_{1-6}$) alkoxycarbonyl, ($C_{1-6}$)alkylcarbonyl, ($C_{2-6}$) alkenyloxycarbonyl or ($C_{2-6}$)alkenylcarbonyl and optionally further substituted by ($C_{1-6}$)alkyl or ($C_{2-6}$)alkenyl; ($C_{1-6}$)alkylsulphonyl; trifluoromethylsulphonyl; ($C_{2-6}$) alkenylsulphonyl; ($C_{1-6}$)alkoxycarbonyl, ($C_{1-6}$) alkylcarbonyl; ($C_{2-6}$)alkenyloxycarbonyl; and ($C_{2-6}$) alkenylcarbonyl;

and $R^{11}$ is hydrogen; or ($C_{1-4}$)alkyl or ($C_{2-4}$)alkenyl optionally substituted with 1 to 3 groups selected from:

carboxy; ($C_{1-4}$)alkoxycarbonyl; ($C_{1-4}$)alkylcarbonyl; ($C_{2-4}$) alkenyloxycarbonyl; ($C_{2-4}$)alkenylcarbonyl; aminocarbonyl wherein the amino group is optionally substituted by hydroxy, ($C_{1-4}$)alkyl, hydroxy($C_{1-4}$)alkyl, aminocarbonyl ($C_{1-4}$)alkyl, ($C_{1-4}$)alkenyl, ($C_{1-4}$)alkylsulphonyl, trifluoromethylsulphonyl, ($C_{2-4}$)alkenylsulphonyl, ($C_{1-4}$) alkoxycarbonyl, ($C_{1-4}$)alkylcarbonyl, ($C_{2-4}$) alkenyloxycarbonyl or ($C_{2-4}$)alkenylcarbonyl; cyano; tetrazolyl; 2-oxo-oxazolidinyl optionally substituted by $R^{10}$; 3-hydroxy-3-cyclobutene-1,2-dione-4-yl; 2,4-thiazolidinedione-5-yl; tetrazol-5-ylaminocarbonyl; 1,2,4-triazol-5-yl optionally substituted by $R^{10}$; 5-oxo-1,2,4-oxadiazol-3-yl; thiol; halogen; ($C_{1-4}$)alkylthio; trifluoromethyl; azido; hydroxy optionally substituted by ($C_{1-4}$)alkyl, ($C_{2-4}$)alkenyl, ($C_{1-4}$)alkoxycarbonyl, ($C_{1-4}$) alkylcarbonyl, ($C_{2-4}$)alkenyloxycarbonyl, ($C_{2-4}$) alkenylcarbonyl; oxo; ($C_{1-4}$)alkylsulphonyl; ($C_{2-4}$) alkenylsulphonyl; or ($C_{1-4}$)aminosulphonyl wherein the amino group is optionally substituted by ($C_{1-4}$)alkyl or ($C_{2-4}$)alkenyl.

This invention also provides a method of treatment of bacterial infections in mammals, particularly in man, which method comprises the administration to a mammal in need of such treatment an effective amount of a compound of formula (I), or a pharmaceutically acceptable derivative thereof.

The invention also provides the use of a compound of formula (I), or a pharmaceutically acceptable derivative thereof, in the manufacture of a medicament for use in the treatment of bacterial infections in mammals.

The invention also provides a pharmaceutical composition comprising a compound of formula (I), or a pharmaceutically acceptable derivative thereof, and a pharmaceutically acceptable carrier.

In one aspect $R^6$ and $R^7$ are not ($C_{1-6}$)alkoxy.

Preferred groups of compounds include those where:

(a) $Z^1$ is N, and $Z^2$–$Z^5$ are CH, (b) $Z^1$–$Z^5$ are each CH, and (c) $Z^5$ is N, and $Z^1$–$Z^4$ are CH, and $Z^3$ may instead be CF.

When $R^1$ or $R^{1a}$ is substituted alkoxy it is preferably ($C_{2-6}$)alkoxy substituted by optionally N-substituted amino, guanidino or amidino, or ($C_{1-6}$)alkoxy optionally substituted by piperidyl. Suitable examples of $R^1$ and $R^{1a}$ alkoxy include methoxy, n-propyloxy, i-butyloxy, aminoethyloxy, aminopropyloxy, aminobutyloxy, aminopentyloxy, guanidinopropyloxy, piperidin-4-ylmethyloxy, phthalimido pentyloxy and 2-aminocarbonylprop-2-oxy.

Preferably $R^1$ and $R^{1a}$ are independently methoxy, amino ($C_{3-5}$)alkyloxy, guanidino($C_{3-5}$)alkyloxy, piperidyl($C_{3-5}$) alkyloxy, nitro or fluoro, more preferably methoxy, amino ($C_{3-5}$)alkyloxy or guanidino($C_{3-5}$)alkyloxy.

$Z^2$ and $Z^4$ are preferably CH.

When $Z^5$ is $CR^{1a}$, $R^{1a}$ is preferably hydrogen, cyano, hydroxymethyl or carboxy.

When $Z^3$ is $CR^{1a}$, $R^{1a}$ is preferably F.

Preferred examples of $R^3$ include hydrogen; ($C_{1-4}$)alkyl; ethenyl; optionally substituted 1-hydroxy($C_{1-4}$)alkyl; carboxy; ($C_{1-6}$)alkoxycarbonyl; optionally substituted aminocarbonyl; carboxy($C_{1-4}$)alkyl; optionally substituted aminocarbonyl($C_{1-4}$)alkyl; cyano($C_{1-4}$)alkyl; optionally substituted 2-oxo-oxazolidinyl and optionally substituted 2-oxo-oxazolidinyl($C_{1-4}$alkyl). More preferred $R^3$ groups are hydrogen; $CONH_2$; 1-hydroxyalkyl e.g. $CH_2OH$, $CH(OH)CH_2CN$; $CH_2CO_2H$; $CH_2CONH_2$; 1,2-dihydroxyalkyl e.g. $CH(OH)CH_2OH$: $CH_2CN$; 2-oxo-oxazolidin-5-yl and 2-oxo-oxazolidin-5-yl($C_{1-4}$alkyl). Most preferably $R^3$ is hydrogen, hydroxymethyl or aminocarbonyl.

$R^3$ is preferably in the 3-position.

In a preferred aspect, when $R^3$ is in the 3-position the substitutents at the 3- and 4-position of the piperidine ring are cis.

When $R^2$ and $R^3$ together form a group $=CR^{5'}R^{6'}$, this is preferably $=CHCH_3$.

Preferably A is CHOH or $CH_2$, more preferably CHOH of R-stereochemistry.

Preferably B is $CH_2$.

Preferably $R^{11}$ is hydrogen or ($C_{1-4}$)alkyl e.g. methyl, more preferably hydrogen.

Preferably $R^4$ is ($C_{5-12}$)alkyl, optionally substituted phenyl($C_{2-3}$)alkyl or optionally substituted phenyl($C_{3-4}$) alkenyl. Suitable groups $R^4$ include n-pentyl, n-hexyl, n-heptyl, n-octyl, n-nonyl, n-decyl, n-dodecyl, phenylethyl, phenylpropyl or 3-phenyl-prop-2-en-yl optionally substituted on the phenyl ring, more preferably $R^4$ is hexyl, heptyl, 5-methylhexyl, 6-methyl heptyl, or 3-phenyl-prop-2-en-yl, especially heptyl.

When used herein, the term "alkyl" includes groups having straight and branched chains, for instance, methyl, ethyl, n-propyl, iso-propyl, n-butyl, iso-butyl, sec-butyl, t-butyl, pentyl and hexyl. The term "alkenyl" should be interpreted accordingly.

Preferred $R^5$ groups are unbranched at the α and, where appropriate, β positions.

Halo or halogen includes fluoro, chloro, bromo and iodo.

Haloalkyl moieties include 1–3 halogen atoms.

The term "heterocyclic" as used herein includes optionally substituted aromatic and non-aromatic, single and fused, rings suitably containing up to four hetero-atoms in each ring selected from oxygen, nitrogen and sulphur, which rings may be unsubstituted or substituted by, for example, up to three groups selected from optionally substituted amino, haloen, $(C_{1-6})$alkyl, $(C_{1-6})$alkoxy, halo$(C_{1-6})$alkyl, hydroxy, carboxy, carboxy salts, carboxy esters such as $(C_{1-6})$ alkoxycarbonyl, $(C_{1-6})$alkoxycarbonyl$(C_{1-6})$alkyl, aryl, and oxo groups. Each heterocyclic ring suitably has from 4 to 7, preferably 5 or 6, ring atoms. A fused heterocyclic ring system may include carbocyclic rings and need include only one heterocyclic ring. Compounds within the invention containing a heterocyclyl group may occur in two or more tautometric forms depending on the nature of the heterocyclyl group; all such tautomeric forms are included within the scope of the invention.

Where an amino group forms part of a single or fused non-aromatic heterocyclic ring as defined above suitable optional substituents in such substituted amino groups include $(C_{1-6})$alkyl optionally substituted by hydroxy, $(C_{1-6})$ alkoxy, thiol, $(C_{1-6})$alkylthio, halo or trifluoromethyl, and amino-protecting groups such as acyl or $(C_{1-6})$ alkylsulphonyl groups.

The term "heteroaryl" includes the aromatic heterocyclic groups referred to above. Examples of heteroaryl groups include pyridyl, triazolyl, tetrazolyl, indolyl, thienyl, isoimidazolyl, thiazolyl, furanyl, quinolinyl, imidazolidinyl and benzothienyl.

When used herein the term "aryl", includes phenyl and naphthyl.

Aryl groups, e.g. phenyl and benzoyl; heteroaryl and heteroaroyl groups may be optionally substituted with up to five, preferably up to three, groups selected from halogen, mercapto, $(C_{1-6})$alkyl, phenyl, $(C_{1-6})$alkoxy, hydroxy$(C_{1-6})$ alkyl, mercapto $(C_{1-6})$alkyl, halo$(C_{1-6})$alkyl, hydroxy, optionally substituted amino, nitro, carboxy, $(C_{1-6})$ alkylcarbonyloxy, $(C_{1-6})$alkoxycarbonyl, formyl, and $(C_{1-6})$ alkylcarbonyl groups.

The term "acyl" includes formyl and $(C_{1-6})$alkylcarbonyl group.

Some of the compounds of this invention may be crystallised or recrystallised from solvents such as aqueous and organic solvents. In such cases solvates may be formed. This invention includes within its scope stoichiometric solvates including hydrates as well as compounds containing variable amounts of water that may be produced by processes such as lyophilisation.

Since the compounds of formula (I) are intended for use in pharmaceutical compositions it will readily be understood that they are each preferably provided in substantially pure form, for example at least 60% pure, more suitably at least 75% pure and preferably at least 85%, especially at least 98% pure (% are on a weight for weight basis). Impure preparations of the compounds may be used for preparing the more pure forms used in the pharmaceutical compositions; these less pure preparations of the compounds should contain at least 1%, more suitably at least 5% and preferably from 10 to 59% of a compound of the formula (I) or pharmaceutically acceptable derivative thereof.

Particular compounds according to the invention include those mentioned in the examples and their pharmaceutically acceptable derivatives.

Pharmaceutically acceptable derivatives of the abovementioned compounds of formula (I) include the free base form or their acid addition or quaternary ammonium salts, for example their salts with mineral acids e.g. hydrochloric, hydrobromic, sulphuric nitric or phosphoric acids, or organic acids, e.g. acetic, fumaric, succinic, maleic, citric, benzoic, p-toluenesulphonic, methanesulphonic, naphthalenesulphonic acid or tartaric acids. Compounds of formula (I) may also be prepared as the N-oxide. Compounds of formula (I) having a free carboxy group may also be prepared as an in vivo hydrolysable ester. The invention extends to all such derivatives.

Examples of suitable pharmaceutically acceptable in vivo hydrolysable ester-forming groups include those forming, esters which break down readily in the human body to leave the parent acid or its salt. Suitable groups of this type include those of part formulae (i), (ii), (iii), (iv) and (v):

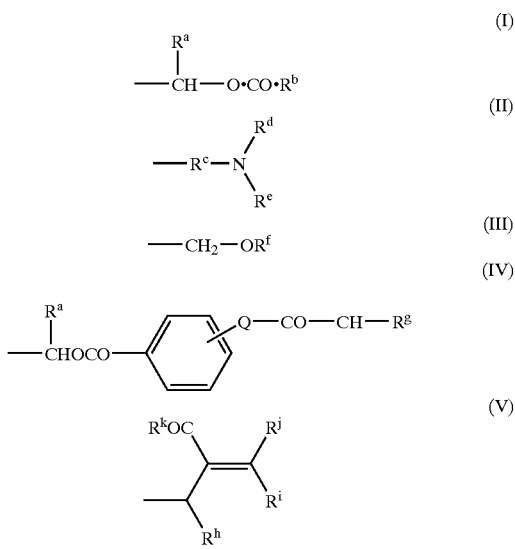

wherein $R^a$ is hydrogen, $(C_{1-6})$ alkyl, $(C_{3-7})$ cycloalkyl, methyl, or phenyl, $R^b$ is $(C_{1-6})$ alkyl, $(C_{1-6})$ alkoxy, phenyl, benzyl, $(C_{3-7})$ cycloalkyl, $(C_{3-7})$ cycloalkyloxy, $(C_{1-6})$ alkyl $(C_{3-7})$ cycloalkyl, 1-amino $(C_{1-6})$ alkyl, or 1-$(C_{1-6}$alkyl) amino $(C_{1-6})$ alkyl; or $R^a$ and $R^b$ together form a 1,2-phenylene group optionally substituted by one or two methoxy groups; $R^c$ represents $(C_{1-6})$ alkylene optionally substituted with a methyl or ethyl group and $R^d$ and $R^e$ independently represent $(C_{1-6})$ alkyl; $R^f$ represents $(C_{1-6})$ alkyl; $R^g$ represents hydrogen or phenyl optionally substituted by up to three groups selected from halogen, $(C_{1-6})$ alkyl, or $(C_{1-6})$ alkoxy; Q is oxygen or NH; $R^h$ is hydrogen or $(C_{1-6})$ alkyl; $R^i$ is hydrogen, $(C_{1-6})$ alkyl optionally substituted by halogen, $(C_{2-6})$ alkenyl, $(C_{1-6})$ alkoxycarbonyl, aryl or heteroaryl; or $R^h$ and $R^i$ together form $(C_{1-6})$ alkylene: $R^j$ represents hydrogen, $(C_{1-6})$ alkyl or $(C_{1-6})$ alkoxycarbonyl; and $R^k$ represents $(C_{1-8})$ alkyl, $(C_{1-8})$ alkoxy, $(C_{1-6})$ alkoxy$(C_{1-6})$alkoxy or aryl.

Examples of suitable in vivo hydrolysable ester groups include, for example, acyloxy$(C_{1-6})$alkyl groups such as acetoxymethyl, pivaloyloxymethyl, α-acetoxyethyl, α-pivaloyloxyethyl, 1-(cyclohexylcarbonyloxy)prop-1-yl, and (1-aminoethyl)carbonyloxymethyl; $(C_{1-6})$ alkoxycarbonyloxy$(C_{1-6})$alkyl groups, such as ethoxycarbonyloxymethyl, α-ethoxycarbonyloxyethyl and propoxycarbonyloxyethyl; di$(C_{1-6})$alkylamino$(C_{1-6})$alkyl especially di$(C_{1-4})$alkylamino$(C_{1-4})$alkyl groups such as dimethylaminomethyl, dimethylaminoethyl, diethylaminomethyl or diethylaminoethyl; 2-(($C_{1-6}$)alkoxycarbonyl)-2-$(C_{2-6})$alkenyl groups such as 2-(isobutoxycarbonyl)pent-2-enyl and 2-(ethoxycarbonyl)but-2-enyl; lactone groups such as phthalidyl and dimethoxyphthalidyl.

A further suitable pharmaceutically acceptable in vivo hydrolysable ester-forming group is that of the formula:

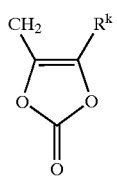

wherein $R^k$ is hydrogen, $C_{1-6}$ alkyl or phenyl.

R is preferably hydrogen.

Compounds of formula (I) may also be prepared as the corresponding N-oxides.

Certain of the compounds of formula (I) may exist in the form of optical isomers, e.g. diastereoisomers and mixtures of isomers in all ratios, e.g. racemic mixtures. The invention includes all such forms, in particular the pure isomeric forms. For example the invention includes compound in which an A-B group CH(OH)—CH$_2$ is in either isomeric configuration, the R-isomer is preferred. The different isomeric forms may be separated or resolved one from the other by conventional methods, or any given isomer may be obtained by conventional synthetic methods or by stereospecific or asymmetric syntheses.

In a further aspect of the invention there is provided a process for preparing compounds of formula (I), and pharmaceutically acceptable derivatives thereof, which process comprises:

reacting a compound of formula (IV) with a compound of formula (V):

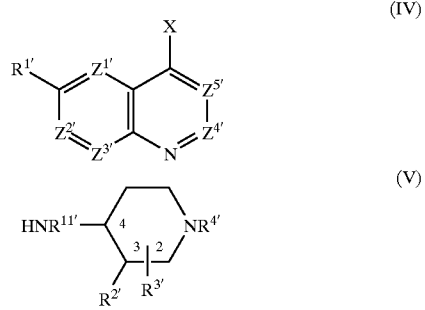

wherein $Z^{1'}$, $Z^{2'}$, $Z^{3'}$, $Z^{4'}$, $Z^{5'}$, $R^{11'}$, $R^{1'}$, $R^{2'}$, $R^{3'}$ and $R^{4'}$ are $Z^1$, $Z^2$, $Z^3$, $Z^4$, $Z^5$, $Z^{11}$, $R^1$, $R^2$, $R^3$ and $R^4$ as defined in formula (I) or groups convertible thereto:
and:
(i) X is $CR^6R^7SO_2W$
(ii) X is A'-COW
(iii) X is $CR^6$=$CH_2$
(iv) X is oxirane
in which W is a leaving group e.g. halogen, A' is A as defined in formula (I), or a group convertible thereto, and oxirane is:

wherein $R^6$ and $R^7$ are as defined in formula (I);
and thereafter optionally or as necessary converting $Z^{1'}$, $Z^{2'}$, $Z^{3'}$, $Z^{4'}$, $Z^{5'}$, A', $R^{11'}$, $R^{1'}$, $R^{2'}$, $R^{3'}$ and $R^{4'}$ to $Z^1$, $Z^2$, $Z^3$, $Z^4$, $Z^5$, A, $R^{11}$, $R^1$, $R^2$, $R^3$ and $R^4$, converting A-B to other A-B, interconverting $R^{11}$, $R^1$, $R^2$, $R^3$ and/or $R^4$ and/or forming a pharmaceutically acceptable derivative thereof.

Process variant (i) initially produces a compound of formula (I) wherein A-B is $CR^6R^7$—$SO_2$.

Process variant (ii) initially produces compounds of formula (I) wherein A-B is A-CO.

Process variant (iii) initially produces compounds of formula (I) wherein A-B is $CHR^6$—$CH_2$.

Process variant (iv) initially produces compounds of formula (I) where A-B is $CR^6(OH)CH_2$.

In process variant (i) the reaction is a standard sulphonamide formation reaction well known to those skilled in the art. This may be e.g. the reaction of a sulphonyl halide with an amine.

In process variant (ii) the reaction is a standard amide formation reaction involving e.g.:
1. Activation of a carboxylic acid (e.g. to an acid chloride, mixed anhydride, active ester. O-acyl-isourea or other species), and treatment with an amine (Ogliaruso, M. A., Wolfe, J. F. in *The Chemistry of Functional Groups* (Ed. Patai, S.) *Suppl. B: The Chemistry of Acid Derivatives*, Pt. 1 (John Wiley and Sons, 1979), pp 442–8; Beckwith, A. L. J. in *The Chemistry of Functional Groups* (Ed. Patai, S.) *Suppl. B: The Chemistry of Amides* (Ed. Zabricky J.) (John Wiley and Sons, 1970), p 73 ff. The acid and amide are preferably reacted in the presence of an activating agent such as 1-(dimethylaminopropyl)-3-ethylcarbodiimide hydrochloride (EDC) or 1-hydroxybenzotriazole (HOBT), or
2. The specific methods of:
a. in situ conversion of an acid into the amine component by a modified Curtius reaction procedure (Shioiri, T., Murata, M., Hamada. Y., *Chem. Pham. Bull.* 1987, 35, 2698)
b. in situ conversion of the acid component into the acid chloride under neutral conditions (Villeneuve, G. B.; Chan. T. H., *Tetrahedron. Lett.* 1997, 38, 6489).

The process variant (iii) is a standard addition reaction using methods well known to those skilled in the art. The process is preferably carried out in a polar organic solvent e.g. acetonitrile in the presence of an organic base e.g. triethylamine.

In process variant (iv) the coupling may be effected in acetonitrile at room temperature in the presence of one equivalent of lithium perchlorate as catalyst (general method of J. E. Chateauneuf et al, *J. Org. Chem.*, 56, 5939–5942). In some cases an elevated temperature such as 40–70° C. may be beneficial. Alternatively, the piperazine may be treated with a base, such as one equivalent of butyl lithium, and the resulting salt reacted with the oxirane in an inert solvent such as tetrahydrofuran, preferably at an elevated temperature such as 80° C. Use of a chiral epoxide will afford single diastereomers. Alternatively, mixtures of diastereomers may be separated by preparative HPLC or by conventional resolution through crystallisation of salts formed from chiral acids.

A hydroxy group on A may be oxidised to a carbonyl group by oxidants well known to those skilled in the art, for example, manganese dioxide, pyridinium chlorochromate or pyridinium dichromate.

A hydroxyalkyl A-B group $CR^6(OH)CH_2$ may be dehydrated to give the group $CR^6$=CH by treatment with an acid anhydride such as acetic anhydride.

Methods for conversion of $CR^6$=CH by reduction to $CHR^6CH_2$ are well known to those skilled in the art, for example using hydrogenation over palladium on carbon as catalyst. Methods for conversion of $CR^6$=CH to give the A-B group $CR^6(OH)CH_2$ are well known to those skilled in the art for example by epoxidation and subsequent reduction by metal hydrides, hydration, hydroboration or oxymercuration.

An amide carbonyl group may be reduced to the corresponding amine using a reducing agent such as lithium aluminium hydride.

A hydroxy group in A may be converted to azido by activation and displacement e.g. under Mitsunobu conditions using hydrazoic acid or by treatment with diphenylphosphorylazide and base, and the azido group in turn may be reduced to amino by hydrogenation.

$R^{11}$ hydrogen groups may be converted to other $R^{11}$ groups by conventional methods well known to those skilled in the art, for example alkyaltion with an alkyl halid in the presence of an inorganic base.

$R^{1'}$, $R^{1'}$, $R^{2'}$, $R^{3'}$ and $R^{4'}$ are preferably $R^{11}$, $R^1$, $R^2$, $R^3$ and $R^4$. $R^{1'}$ is preferably methoxy. $R^{2'}$ is preferably hydrogen. $R^{3'}$ is preferably $R^3$ such as hydrogen, vinyl, $(C_{1-6})$ alkoxycarbonyl, $CONH_2$, $CH_2OH$, $CH_2CO_2H$, $CH_2CONH_2$, $CH(OH)CH_2OH$, $CH(OH)CH_2CN$, $CH_2CN$, 2-oxo-oxazolidin-5-yl and 2-oxo-oxazolidin-5-yl($C_{1-4}$alkyl), more preferably hydrogen, vinyl or $(C_{1-6})$alkoxycarbonyl,. $R^{4'}$ is preferably heptyl or an N-protecting group such as tert-butoxycarbonyl.

Conversions of $R^{1'}$, $R^{2'}$, $R^{3'}$ and $R^{4'}$ and interconversions of $R^1$, $R^2$, $R^3$ and $R^4$ are conventional. In compounds which contain an optionally protected hydroxy group, suitable conventional hydroxy protecting groups which may be removed without disrupting the remainder of the molecule include acyl and alkylsilyl groups.

For example $R^{1'}$ methoxy is convertible to $R^{1'}$ hydroxy by treatment with lithium and diphenylphosphine (general method described in Ireland et al, *J. Amer. Chem. Soc.*, 1973, 7829) or HBr. Alkylation of the hydroxy group with a suitable alkyl derivative bearing a leaving group such as halide and a protected amino, piperidyl, amidino or guanidino group or group convertible thereto, yields, after conversion/deprotection, $R^1$ alkoxy substituted by optionally N-substituted amino, piperidyl, guanidino or amidino.

$R^3$ alkenyl is convertible to hydroxyalkyl by hydroboration using a suitable reagent such as 9-borabicyclo[3.3.1] nonane, epoxidation and reduction or oxymercuration.

$R^3$ 1,2-dihydroxyalkyl can be prepared from $R^{3'}$ alkenyl using osmium tetroxide or other reagents well known to those skilled in the art (see Advanced Organic Chemistry, Ed. March, J., John Wiley and Sons, 1985, p 732–737 and refs. cited therein) or epoxidation followed by hydrolysis (see Advanced Organic Chemistry, Ed. March, J. John Wiley and Sons, 1985, p 332,333 and refs. cited therein).

$R^3$ vinyl can be chain extended by standard homologation, e.g. by conversion to hydroxyethyl followed by oxidation to the aldehyde, which is then subjected to a Wittig reaction.

Opening an epoxide-containing $R^{3'}$ group with cyanide anion yields a CH(OH)—$CH_2CN$ group.

Opening an epoxide-containing $R^{3'}$ group with azide anion yields an azide derivative which can be reduced to the amine. Conversion of the amine to a carbamate is followed by ring closure with base to give the 2-oxo-oxazolidinyl containing $R^3$ group.

Substituted 2-oxo-oxazolidinyl containing $R^3$ groups may be prepared from the corresponding aldehyde by conventional reaction with a glycine anion equivalent, followed by cyclisation of the resulting amino alcohol (M. Grauert et al, *Ann. Chem.*, 1985, 1817; Rozenberg et al, *Angew. Chem. Int. Ed. Engl.*, 1994, 33(1), 91). The resulting 2-oxo-oxazolidinyl group contains a carboxy group which can be converted to other $R^{10}$ groups by standard procedures.

Carboxy groups within $R^3$ may be prepared by Jones' oxidation of the corresponding alcohols $CH_2OH$ using chromium acid and sulphuric acid in water/methanol (E. R. H. Jones et al, *J. Chem. Soc.*, 1946, 39). Other oxidising agents may be used for this transformation such as sodium periodate catalysed by ruthenium trichloride (G. F. Tutwiler et al, *J. Med. Chem.*, 1987, 30(6), 1094), chromium trioxide-pyridine (G. Just et al, *Synth. Commun.*, 1979, 9(7), 613), potassium permanganate (D. E. Reedich et al. *J. Org. Chem.*, 1985, 50(19), 3535), and pyridinium chlorochromate (D. Askin et al, *Tetrahedron Lett.*, 1988, 29(3), 277).

Other routes to the synthesis of carboxy groups within $R^3$ are well known to those skilled in the art.

$R^3$ groups containing a cyano group may be prepared by conversion of an alcohol to a suitable leaving group such as the corresponding tosylate by reaction with para-toluenesulphonyl chloride (M. R. Bell, *J. Med. Chem.*, 1970, 13, 389), or the iodide using triphenylphosphine, iodine, and imidazole (G. Lange, *Synth. Commun.*, 1990, 210, 1473). The second stage is the displacement of the leaving group with cyanide anion (L. A. Paquette et al, *J. Org. Chem.*, 1979, 44(25), 4603; P. A. Grieco et al, *J. Org. Chem.*, 1988, 53(16), 3658). Other functional groups in $R^3$ may be obtained by conventional conversions of carboxy or cyano groups.

Tetrazoles are conveniently prepared by reaction of sodium azide with the cyano group (e.g. F. Thomas et al, *Bioorg. Med. Chem. Lett.*, 1996, 6(6), 631; K. Kubo et al, *J. Med. Chem.*, 1993, 36, 2182) or by reaction of azidotri-n-butyl stannane with the cyano group followed by acidic hydrolysis (P. L. Ornstein, *J. Org. Chem.*, 1994, 59, 7682 and *J. Med. Chem*, 1996, 39 (11), 2219).

The 3-hydroxy-3-cyclobutene-1,2-dion-4-yl group (e.g. R. M. Soll, *Bioorg. Med. Chem. Lett.*, 1993, 3(4), 757 and W. A. Kinney, *J. Med. Chem.*, 1992, 35(25), 4720) can be prepared by the following sequence:—(1) a compound where $R^3$ is $(CH_2)_n$CHO (n=0,1,2) is treated with triethylamine, carbontetrabromide-triphenylphosphine to give initially $(CH_2)_n$CH=CHBr; (2) dehydrobromination of this intermediate to give the corresponding bromoethyne derivative $(CH_2)_n$C≡CBr (for this 2 stage sequence see D. Grandjean et al, *Tetrahedron Lett.*, 1994. 35(21), 3529); (3) palladium-catalysed coupling of the bromoethyne with 4-(1-methylethoxy)-3-(tri-n-butylstannyl)cyclobut-3-ene-1,2-dione (Liebeskind et al, *J. Org. Chem.*, 1990, 55, 5359); (4) reduction of the ethyne moiety to —$CH_2CH_2$— under standard conditions of hydrogen and palladium on charcoal catalysis(see Howard et al. *Tetrahedron*, 1980, 36, 171); and finally (4) acidic hydrolysis of the methylethoxyester to generate the corresponding 3-hydroxy-3-cyclobutene-1,2-dione group (R. M. Soll, *Bioorg. Med. Chem. Lett.*, 1993, 3(4), 757).

The tetrazol-5-ylaminocarbonyl group may be prepared from the corresponding carboxylic acid and 2-aminotetrazole by dehydration with standard peptide coupling agents such as 1,1'-carbonyldiimidazole (P. L. Ornstein et al, *J. Med Chem*, 1996, 39(11), 2232).

The alkyl- and alkenyl-sulphonylcarboxamides are similarly prepared from the corresponding carboxylic acid and the alkyl- or alkenyl-sulphonamide by dehydration with standard peptide coupling agents such as 1,1'-carbonyldiimidazole (P. L. Ornstein et al, *J. Med. Chem.*, 1996, 39(11), 2232).

The hydroxamic acid groups are prepared from the corresponding acids by standard amide coupling reactions e.g. N. R. Patel et al, *Tetrahedron*, 1987, 43(22), 5375.

2,4-Thiazolidinedione groups may prepared from the aldehydes by condensation with 2,4-thiazolidinedione and subsequent removal of the olefinic double bond by hydrogenation.

The preparation of 5-oxo-1,2,4-oxadiazoles from nitrites is decribed by Y. Kohara et al, *Bioorg. Med. Chem. Lett.,* 1995, 5(17), 1903.

1,2,4-Triazol-5-yl groups may be prepared from the corresponding nitrile by reaction with an alcohol under acid conditions followed by reaction with hydrazine and then an $R^{10}$-substituted activated carboxylic acid (see J. B. Polya in "Comprehensive Heterocyclic Chemistry" Edition 1, p762, Ed A. R. Katritzky and C. W. Rees, Pergamon Press. Oxford, 1984 and J. J. Ares et al, *J. Heterocyclic Chem.,* 1991, 28(5), 1197).

Other substituents on $R^3$ alkyl or alkenyl may be interconverted by conventional methods, for example hydroxy may be derivatised by esterification, acylation or etherification. Hydroxy groups may be converted to halogen, thiol, alkylthio, azido, alkylcarbonyl, amino, aminocarbonyl, oxo, alkylsulphonyl, alkenylsulphonyl or aminosulphonyl by conversion to a leaving group and substitution by the required group or oxidation as appropriate or reaction with an activated acid, isocyanate or alkoxyisocyanate. Primary and secondary hydroxy groups can be oxidised to an aldehyde or ketone respectively and alkylated with a suitable agent such as an organometallic reagent to give a secondary or tertiary alcohol as appropriate.

Compounds of formula (I) where $R^2$ and $R^3$ are a divalent residue $=CR^{51}R^{61}$ can be prepared by treatment of a compound of formula (I) where $R^3$ is alken-1-yl with a strong base in an aprotic solvent. Suitable bases include $Ph_2PLi$/PhLi (as described in Ireland et al, *J. Amer. Chem. Soc.,* 1973, 7829), t-BuLi, and suitable solvents include THF and ether.

Piperidine N-protecting groups are removed by conventional methods and NH is converted to $NR^4$ by conventional means such as alkylation with an alkyl halide in the presence of base, acylation/reduction or reductive alkylation with an aldehyde.

It will be appreciated that under certain circumstances interconversions may interfere, for example, A or B hydroxy groups in A or B and the piperidine NH will require protection e.g. as a carboxy- or silyl-ester group for hydroxy and as an acyl derivative for piperidine nitrogen, during conversion of $R^{1'}$, $R^{2'}$, $R^{3'}$ or $R^{4'}$.

Compounds of formula (IV) where X is $CR^6R^7SO_2W$ may be prepared by a route analogous to that of Ahmed El Hadri et al, *J. Heterocyclic Chem.,* 1993, 30(3), 631. Thus compounds of formula (IV) where X is $CH_2SO_2OH$ may be prepared by reacting the corresponding 4-methyl compound with N-bromosuccinimide, followed by treatment with sodium sulfite. The leaving group W may be converted to another leaving group W, e.g. a halogen group, by conventional methods.

4-Alkenyl compounds of formula (IV) may be prepared by conventional procedures from a corresponding 4-halogeno-derivative by e.g. a Heck synthesis as described in e.g. *Organic Reactions,* 1982, 27, 345.

4-Halogeno derivatives of compounds of formula (IV) are commercially available, or may be prepared by methods known to those skilled in the art. A 4-chloroquinoline is prepared from the corresponding quinolin-4-one by reaction with phosphorus oxychloride ($POCl_3$) or phosphorus pentachloride, $PCl_5$. A 4-chloroquinazoline is prepared from the corresponding quinazolin-4-one by reaction with phosphorus oxychloride ($POCl_3$) or phosphorus pentachloride, $PCl_5$. A quinazolinone and quinazolines may be prepared by standard routes as described by T. A. Williamson in *Heterocyclic Compounds,* 6, 324 (1957) Ed. R. C. Elderfield.

The 4-methyl derivatives of compounds of formula (IV) may be prepared by Stille reactions of the 4-halogeno derivatives with tetramethyl tin (Sile, Angewandte International Edition Engl., 1986, 25, 508).

Activated carboxy derivatives X=A'COW of formula (IV) may be prepared from $X=A'CO_2H$ derivatives in turn prepared from $CO_2H$ derivatives by conventional methods such as homologation.

A 4-oxirane compound of formula (IV) is conveniently prepared from the 4-carboxylic acid by first conversion to the acid chloride with oxalyl chloride and then reaction with trimethylsilyldiazomethane to give the diazoketone derivative. Subsequent reaction with 5M hydrochloric acid gives the chloromethylketone. Reduction with sodium borohydride in aqueous methanol gives the chlorohydrin which undergoes ring closure to afford the epoxide on treatment with base, e.g. potassium hydroxide in ethanol-tetrahydrofuran.

If a chiral reducing agent such as (+) or (−)-B-chlorodiisopinocamphenylborane [DIP-chloride] is substituted for sodium borohydride, the prochiral chloromethylketone is converted into the chiral chlorohydrin with ee values generally 85–95% [see C. Bolm et al, *Chem. Ber.* 125, 1169–1190, (1992)]. Recrystallisation of the chiral epoxide gives material in the mother liquor with enhanced optical purity (typically ee 95%).

The (R)-epoxide, when reacted with a piperazine derivative gives ethanolamine compounds as single diastereomers with (R)-stereochemistry at the benzylic position.

4-Carboxy derivatives of compounds of formula (IV) are commercially available or may be prepared by conventional procedures for preparation of carboxy heteroaromatics well known to those skilled in the art. For example, quinazolines may be prepared by standard routes as described by T. A. Williamson in *Heterocyclic Compounds,* 6, 324 (1957) Ed. R. C. Elderfield, Pyridazines and napthyridines may be prepared by routes analogous to those described in *Comprehensive Heterocyclic Chemistry*, Volumes 2 & 3, Ed A. J. Boulton and A. McKillop. These 4-carboxy derivatives may be activated by conventional means, e.g. by conversion to an acyl halide or anhydride.

Alternatively, the epoxide may be prepared from the 4-carboxaldehyde by a Wittig approach using trimethylsulfonium iodide [see G. A. Epling and K-Y Lin,*J. Het. Chem.,* 1987, 24, 853–857], or by epoxidation of a 4-vinyl derivative.

4-Hydroxy-1,5-naphthyridines can be prepared from 3-aminopyridine derivatives by reaction with diethyl ethoxymethylene malonate to produce the 4-hydroxy-3-carboxylic acid ester derivative with subsequent hydrolysis to the acid, followed by thermal decarboxylation in quinoline (as for example described for 4-Hydroxy-[1,5] naphthyridine-3-carboxylic acid, Joe T. Adams et al., *J.Amer.Chem.Soc.,* 1946. 68, 1317). A 4-hydroxy-[1,5] naphthyridine can be converted to the 4-chloro derivative by heating in phosphorus oxychloride. Similarly, 6-methoxy-1, 5-naphthyridine derivatives can be prepared from 3-amino-6-methoxypyridine.

1,5-Naphthyridines may be prepared by other methods well known to those skilled in the art (for examples see P. A. Lowe in "Comprehensive Heterocyclic Chemistry" Volume 2, p581–627, Ed A. R. Katritzky and C. W. Rees, Pergamon Press, Oxford, 1984).

The 4-hydroxy-cinnolines may be prepared following methods well known to those skilled in the art [see A. R. Osborn and K. Schofield, *J. Chem. Soc.* 2100 (1955)]. For example, a 2-aminoacetopheneone is diazotised with sodium nitrite and acid to produce the 4-hydroxycinnoline with conversion to chloro and amino derivatives as described for 1.5-naphthyridines.

For compounds of formula (V), suitable amines may be prepared from the corresponding 4-substituted piperidine acid or alcohol. In a first instance, an N-protected piperidine containing an acid bearing substituent, can undergo a Curtius rearrangement and the intermediate isocyanate can be converted to a carbamate by reaction with an alcohol. Conversion to the amine may be achieved by standard methods well known to those skilled in the art used for amine protecting group removal. For example, an acid substituted N-protected piperidine can undergo a Curtius rearrangement e.g. on treatment with diphenylphosphoryl azide and heating, and the intermediate isocyanate reacts in the presence of 2-trimethylsilylethanol to give the trimethylsilylethylcarbamate (T. L. Capson & C. D. Poulter, *Tetrahedron Lett.*, 1984, 25, 3515). This undergoes cleavage on treatment with tetrabutylammonium fluoride to give the 4-amine substituted N-protected piperidine.

In a second instance, an N-protected piperidine containing an alcohol bearing substituent undergoes a Mitsunobu reaction (for example as reviewed in Mitsunobu, *Synthesis*, (1981), 1), for example with succinimide in the presence of diethyl azodicarboxylate and triphenylphosphine to give the phthalimidoethylpiperidine. Removal of the phthaloyl group, for example by treatment with methylhydrazine, gives the amine of formula (V).

Conversions of $R^{1'}$, $R^{2'}$, $R^{3'}$ and $R^{4'}$ may be carried out on the intermediates of formulae (IV), and (V) prior to their reaction to produce compounds of formula (I) in the same way as described above for conversions after their reaction.

Further details for the preparation of compounds of formula (I) are found in the examples.

The compounds of formula (I) may be prepared singly or as compound libraries comprising at least 2, for example 5 to 1,000 compounds, and more preferably 10 to 100 compounds of formula (I). Libraries of compounds of formula (I) may be prepared by a combinatorial 'split and mix' approach or by multiple parallel synthesis using either solution phase or solid phase chemistry, by procedures known to those skilled in the art.

Thus according to a further aspect of the invention there is provided a compound library comprising at least 2 compounds of formula (I) or pharmaceutically acceptable derivatives thereof.

Novel intermediates of formulae (IV) and (V) are also part of this invention.

The antibacterial compounds according to the invention may be formulated for administration in any convenient way for use in human or veterinary medicine, by analogy with other antibacterials.

The pharmaceutical compositions of the invention include those in a form adapted for oral, topical or parenteral use and may be used for the treatment of bacterial infection in mammals including humans.

The composition may be formulated for administration by any route. The compositions may be in the form of tablets, capsules, powders, granules, lozenges, creams or liquid preparations, such as oral or sterile parenteral solutions or suspensions.

The topical formulations of the present invention may be presented as, for instance, ointments, creams or lotions, eye ointments and eye or ear drops, impregnated dressings and aerosols, and may contain appropriate conventional additives such as preservatives, solvents to assist drug penetration and emollients in ointments and creams.

The formulations may also contain compatible conventional carriers, such as cream or ointment bases and ethanol or oleyl alcohol for lotions. Such carriers may be present as from about 1% up to about 98% of the formulation. More usually they will form up to about 80% of the formulation.

Tablets and capsules for oral administration may be in unit dose presentation form, and may contain conventional excipients such as binding agents, for example syrup, acacia, gelatin, sorbitol, tragacanth, or polyvinylpyrrolidone; fillers, for example lactose, sugar, maize-starch, calcium phosphate, sorbitol or glycine; tabletting lubricants, for example magnesium stearate, talc, polyethylene glycol or silica; disintegrants, for example potato starch; or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives, such as suspending agents, for example sorbitol, methyl cellulose, glucose syrup, gelatin, hydroxyethyl cellulose, carboxymethyl cellulose, aluminium stearate gel or hydrogenated edible fats, emulsifying agents, for example lecithin, sorbitan monooleate, or acacia; non-aqueous vehicles (which may include edible oils), for example almond oil, oily esters such as glycerine, propylene glycol, or ethyl alcohol; preservatives, for example methyl or propyl p-hydroxybenzoate or sorbic acid, and, if desired, conventional flavouring or colouring agents.

Suppositories will contain conventional suppository bases, e.g. cocoa-butter or other glyceride.

For parenteral administration, fluid unit dosage forms are prepared utilizing the compound and a sterile vehicle, water being preferred. The compound, depending on the vehicle and concentration used, can be either suspended or dissolved in the vehicle. In preparing solutions the compound can be dissolved in water for injection and filter sterilised before filling into a suitable vial or ampoule and sealing.

Advantageously, agents such as a local anaesthetic, preservative and buffering agents can be dissolved in the vehicle. To enhance the stability, the composition can be frozen after filling into the vial and the water removed under vacuum. The dry lyophilized powder is then sealed in the vial and an accompanying vial of water for injection may be supplied to reconstitute the liquid prior to use. Parenteral suspensions are prepared in substantially the same manner except that the compound is suspended in the vehicle instead of being dissolved and sterilization cannot be accomplished by filtration. The compound can be sterilised by exposure to ethylene oxide before suspending in the sterile vehicle. Advantageously, a surfactant or wetting agent is included in the composition to facilitate uniform distribution of the compound.

The compositions may contain from 0.1% by weight, preferably from 10–60% by weight, of the active material, depending on the method of administration. Where the compositions comprise dosage units, each unit will preferably contain from 50–500 mg of the active ingredient. The dosage as employed for adult human treatment will preferably range from 100 to 3000 mg per day, for instance 1500 mg per day depending on the route and frequency of administration. Such a dosage corresponds to 1.5 to 50 mg/kg per day. Suitably the dosage is from 5 to 20 mg/kg per day.

No toxicological effects are indicated when a compound of formula (I) or a pharmaceutically acceptable derivative thereof is administered in the above-mentioned dosage range.

The compound of formula (I) may be the sole therapeutic agent in the compositions of the invention or a combination with other antibacterials. If the other antibacterial is a β-lactam then a β-lactamase inhibitor may also be employed.

Compounds of formula (I) are active against a wide range of organisms including both Gram-negative and Gram-positive organisms.

All publications, including but not limited to patents and patent applications, cited in this specification are herein incorporated by reference as if each individual publication were specifically and individually indicated to be incorporated by reference herein as though fully set forth.

The following examples illustrate the preparation of certain compounds of formula (I) and the activity of certain compounds of formula (I) against various bacterial organisms.

EXAMPLE 1

1-Heptyl-4-[2-(R)-hydroxy-2-(6-methoxyquinolin-4-yl)]ethylaminopiperidine dioxalate

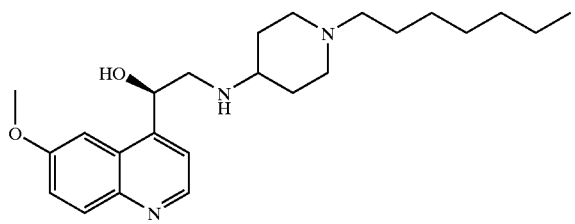

(a) [R]-2-(6-Methoxyquinolin-4-yl)oxirane

A solution of 6-methoxyquinoline-4-carboxylic acid (10 g) in dichloromethane was heated under reflux with oxalyl chloride (5 ml) and dimethylformamide (2 drops) for 1 hour and evaporated to dryness. The residue, in dichloromethane (100 ml) was treated with a 2M solution of trimethylsilyl-diazomethane in hexane (50 ml) and stirred at room temperature for 18 hours. 5M Hydrochloric acid (150 ml) was added and the solution was stirred at room temperature for 3 hours. It was basified with sodium carbonate solution, extracted with ethyl acetate and chromatographed on silica gel eluting with ethyl acetate-hexane to give the chloromethyl ketone (4.2 g). A batch of the chloromethyl ketone (20 g) was reduced with (+)-B-chlorodiisopinocamphenylborane (40 g) in dichloromethane (400 ml) at room temperature for 18 hours followed by treatment with diethanolamine (30 g) for 3 hours. The product was chromatographed on silica gel eluting with ethyl acetate-hexane to give the chloroalcohol (16.8 g), which was dissolved in tetrahydrofuran (100 ml) and reacted with sodium hydroxide (2.6 g) in water (13 ml) for 1.5 hours. The reaction mixture was evaporated to dryness and chromatographed on silica gel eluting with ethyl acetate-hexane to give the title compound as a solid (10.4 g) (84% ee by chiral HPLC). Recrystallisation from ether-pentane gave mother-liquor (7.0 g) (90% ee).

MS (+ve ion electrospray) m/z 202 (MH+)

The absolute stereochemistry was defined to be (R) by an NMR study on the Mosher's esters derived from the product obtained by reaction with 1-t-butylpiperazine.

(b) 4-Benzyloxycarbonyl-1-tert-butoxycarbonylpiperidine

A solution of 1-tert-butoxycarbonyl-piperidine-4-carboxylic acid (20 g) in DMF (100 ml) was treated with anhydrous potassium carbonate (60 g) and then benzyl bromide (16.43 g) and the mixture was stirred at room temperature for 72 hours. It was filtered, evaporated to dryness, dissolved in ethyl acetate, washed with sodium carbonate solution and water and dried over sodium sulfate. The product was evaporated to give an oil (29 g).

(c) 1-Heptyl-4-benzyloxycarbonyl-piperidine

The ester (1b) was treated with trifluoroacetic acid in dichloromethane for 3.5 hours and then evaporated to dryness. The product was alkylated with heptyl iodide (22.6 g) in DMF (100 ml) containing potassium carbonate (50.2 g), and was chromatographed on silica gel (ethyl acetate-hexane) to afford an oil (32 g).

(d) 4-Benzyloxycarbonylamino-1-heptyl-piperidine

The ester (1c) (5 g) was hydrogenated in ethanol over 10% palladium-carbon and the dried product was heated with diphenylphosphoryl azide (6.36 g) in refluxing toluene (50 ml) containing benzyl alcohol (8.3 g) and triethylamine (2.35 g) for 18 hours. The product was chromatographed on silica gel (ethyl acetate-hexane) to afford a solid (3.3 g).

MS (+ve ion electrospray) m/z 333 (MH+).

(e) 4-Amino-1-heptylpiperidine

The carbamate (1d) (3.3 g) was hydrogenated in ethanol over 10% palladium-carbon to afford an oil (1.8 g).

(f) Title Compound

A solution of [R]-2-(6-methoxyquinolin-4-yl)oxirane (1a) (0.25 g) and amino-piperidine (1e) (0.295 g) in acetonitrile (3 ml) containing lithium perchlorate (0.131 g) was heated at 50° C. for 18 hours and evaporated to dryness. The product was dissolved in dichloromethane, washed with sodium carbonate, dried over sodium sulfate, and chromatographed on silica gel (methanol-dichloromethane) to afford the title compound (0.085 g) as the oily free base.

MS (+ve ion electrospray) m/z 400 (MH+).

The oil was treated with 2 molar equivalents of oxalic acid in ether and the resulting solid was collected, triturated with ether, to afford the dioxalate salt as a white solid.

EXAMPLE 2 cis-3-(R/S)-Ethoxycarbonyl-1-heptyl-4(S/R)-[2-(R)-hydroxy-2-(6-methoxyquinolin-4-yl)]ethylaminopiperidine dioxalate

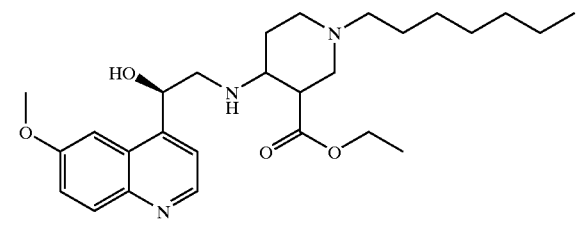

(a) 4-Benzylamino-1-tert-butoxycarbonyl-3-ethoxycarbonyl-1,2,5,6-tetrahydropyridine A solution of 1-tert-butoxycarbonyl-3-ethoxycarbonylpiperidin-4-one (prepared from 3-ethoxycarbonylpiperidin-4-one and di-tert-butyl-dicarbonate in dichloromethane and triethylamine) (25 g) and benzylamine (10.85 g) in toluene was heated under reflux in a Dean and Stark apparatus for 18 hours and then evaporated to dryness to give an oil.

(b) cis-4-(S/R)-Benzylamino-1-tert-butoxycarbonyl-3-(R/S)-ethoxycarbonylpiperidine The enamine (2a)(25 g) in ethanol (300 ml) was hydrogenated over platinum oxide (1.5 g) for 4 days, filtered, and evaporated to dryness. It was chromatographed on silica gel (ethyl acetate-hexane) to afford the title compound as an oil.

MS (+ve ion electrospray) m/z 363 (MH+).

(c) cis-4-(S/R)-Amino-1-tert-butoxycarbonyl-3-(R/S)-ethoxycarbonylpiperidine

The amine (2b) (4 g) in ethanol (80 ml) containing acetic acid (0.73 g) was hydrogenated at 50 psi (Parr reaction vessel) over 10% palladium-carbon (1 g) for 18 hours, filtered and evaporated to dryness to afford the acetate salt of the title compound as a white solid (3 g).

MS (+ve ion electrospray) m/z 273 (MH+).

It was converted to the oily free base by extraction using dichloromethane-sodium carbonate and drying over sodium sulfate.

(d) cis-1-tert-Butoxycarbonyl-3-(R/S)-ethoxycarbonyl-4-(S/R)-[2-(R)-hydroxy-2-(6-methoxyquinolin-4-yl)]ethylaminopiperidine A solution of [R]-2-(6-methoxyquinolin-4-yl)oxirane (1a) (0.273 g) and the piperidine (2c) (0.37 g) in acetonitrile (5 ml) containing lithium perchlorate (0.144 g) was heated at 40° C. for 72 hours and evaporated to dryness. The product was dissolved in dichloromethane, washed with sodium carbonate, dried over sodium sulfate, and chromatographed on silica gel (ethyl acetate-hexane) to afford the title compound (0.34 g).

MS (+ve ion electrospray) m/z 474 (MH+).

(e) cis-3-(R/S)-Ethoxycarbonyl-4-(S/R)-[2-(R)-hydroxy-2-(6-methoxyuinolin-4-yl)]ethylaminopiperidine The amine (2d) was treated with dichloromethane (20 ml) and trifluoroacetic acid (20 ml) at room temperature for 3 hours and evaporated to dryness. It was basified with sodium carbonate solution, extracted with dichloromethane, dried over sodium sulfate and evaporated to afford an oil (0.19 g).

(f) Title Compound

The amine (2e) in dry methanol (3 ml) was treated with heptaldehyde (0.059 g) and sodium triacetoxyborohydride (0.107 g) for 1 hour at room temperature. Sodium bicarbonate solution was added and the mixture was extracted with dichloromethane, dried over sodium sulfate, and evaporated to afford an oil. Chromatography on silica gel (ethyl acetate-hexane) gave the title compound (0.15 g) as an oil.

MS (+ve ion electrospray) m/z 472 (MH+).

EXAMPLE 3 cis-3-(R/S)-Aminocarbonyl-1-heptyl-4-(S/R)-[2-(R)-hydroxy-2-(6-methoxyquinolin-4-yl)]ethylaminopiperidine dioxalate

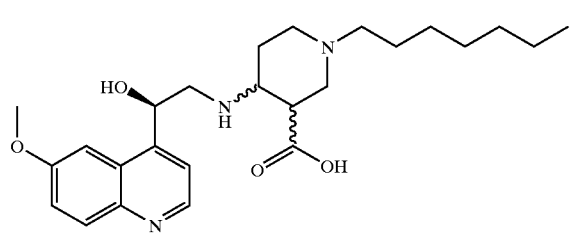

The ester Example 2 (0.16 g) in ethanol (3 ml) was heated with ammonia (3 ml) at 50° C. (sealed bomb) for 6 days and evaporated to dryness. Chromatography on silica (ethyl-acetate-hexane then methanol-dichloromethane) gave the title compound (0.05 g), as the free base.

MS (+ve ion electrospray) m/z 443 (MH+).

$^1$H NMR (CDCl$_3$) δ: 0.88 (3H, t), 1.30 (9H, bs), 1.47 (2H, bs), 1.75 (1H, bt), 1.95–2.80 (~8H, m), 2.98 (2H, m), 3.85 (1H, m), 3.95 (3H, s), 4.25 (1H, bt), 5.41 (1H, m) 7.17 (1H, bs), 7.39 (1H, dd), 7.65 (1H, d), 8.05 (1H, d), 8.78 (1H, d).

The free base in dichloromethane was treated with 2 molar equivalents of oxalic acid in ether and the resulting solid was collected, triturated with ether, to afford the dioxalate salt as a white solid.

EXAMPLE 4 cis-1-Heptyl-3-(R/S)-hydroxymethyl-4-(S/R)-[2-(R)-hydroxy-2-(6-methoxyquinolin-4-yl)]ethylaminopiperidine dioxalate

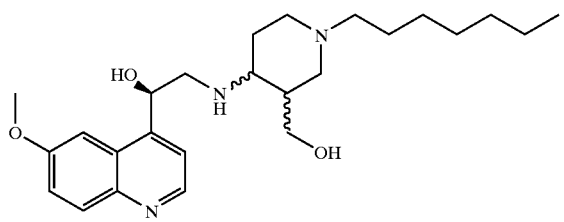

The ester Example 2 (0.13 g) in dry tetrahydrofuran (3 ml) at −10° C. was treated with lithium aluminium hydride (0.28 ml of a 1M solution in ether) for 3 hours and then quenched by the addition of 2M sodium hydroxide. Dichloromethane and sodium sulfate were added and the solution was filtered and evaporated to dryness. The product was chromatographed on silica gel (methanol-dichloromethane) to afford the title compound (0.04 g), as the oily free base.

MS (+ve ion electrospray) m/z 430 (MH+).

$^1$H NMR (CDCl$_3$) δ: 0.88 (3H, t), 1.30 (9H, bs), 1.45 (2H, bs), 1.9 (3H, m), 2.25 (3H, m), 2.5–3.3 (8H, m), 3.8 (5H, bd), 5.38 (1H, m) 7.20 (1H, m), 7.39 (1H, dd), 7.55 (1H,m), 8.05 (1H, dd), 8.78 (1H, d).

The free base in dichloromethane was converted to the dioxalate salt in the normal manner, affording a white solid.

The following compound Examples were prepared following the procedures described in the synthetic methodology section and previous preparative Examples:

EXAMPLE 5 cis-3-(R/S)-carboxy-1-heptyl-4-(S/R)-[2-(R)-hydroxy-2-(6-methoxyquinolin-4-yl)]ethylaminopiperidine tris-trifluoroacetate MS (+ve ion electrospray) m/z 444 (MH+).

EXAMPLE 6

1-Heptyl-4-[2-(S)-hydroxy-2-(6-methoxyquinolin-4-yl)]ethylaminopiperidine dioxalate MS (+ve ion electrospray) m/z 400 (MH+).

EXAMPLE 7

1-Heptyl-4-[2-(R)-hydroxy-2-(6-methoxyquinolin-4-yl)]ethyl(N-methyl)aminopiperidine dioxalate MS (+ve ion electrospray) m/z 414 (MH+).

Biological Activity

The MIC (μg/ml) of test compounds against various organisms was determined: *S. aureus* Oxford, *S. aureus* WCUH29, *S. pneumoniae* 1629, *S. pneumoniae* N1387, *S. pneumoniae* ERY 2.

Examples 1–4 have an MIC of less than or equal to 1 μg/ml against one or more of the above range of gram positive and gram negative bacteria.

What is claimed is:

1. A compound of formula (I) or a pharmaceutically acceptable derivative thereof:

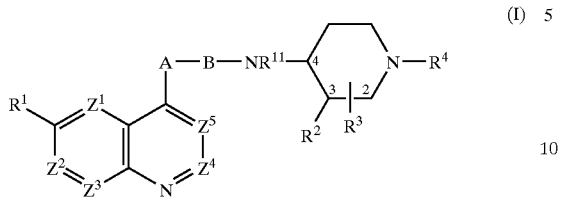

wherein:
one of $Z^1$, $Z^2$, $Z^3$, $Z^4$ and $Z^5$ is N, one is $CR^{1a}$, and the remainder are CH, or one of $Z^1$, $Z^2$, $Z^3$, $Z^4$ and $Z^5$ is $CR^{1a}$, and the remainder are CH;

$R^1$ and $R^{1a}$ are independently hydrogen; hydroxy; $(C_{1-6})$alkoxy optionally substituted by $(C_{1-6})$alkoxy, amino, piperidyl, guanidino or amidino optionally N-substituted by one or two $(C_{1-6})$alkyl, acyl or $(C_{1-6})$alkylsulphonyl groups, $CONH_2$, hydroxy, thiol, $(C_{1-6})$alkylthio, heterocyclylthio, heterocyclyloxy, arylthio, aryloxy, acyloxy or $(C_{1-6})$alkylsulphonyloxy; $(C_{1-6})$alkoxy-substituted$(C_{1-6})$alkyl; halogen: $(C_{1-6})$alkyl; $(C_{1-6})$alkylthio; nitro; azido; acyl; acyloxy; acylthio; $(C_{1-6})$alkylsulphonyl; $(C_{1-6})$alkylsulphoxide; arylsulphonyl; arylsulphoxide or an amino, piperidyl, guanidino or amidino group optionally N-substituted by one or two $(C_{1-6})$alkyl, acyl or $(C_{1-6})$alkylsulphonyl groups;

provided that when one of $Z^1$, $Z^2$, $Z^3$, $Z^4$ and $Z^5$ is $CR^{1a}$ and the remainder are CH, then $R^1$ is not hydrogen;

$R^2$ is hydrogen;

$R^3$ is hydrogen; or $R^3$ is in the 2-, 3- or 4-position and is:

carboxy; $(C_{1-6})$alkoxycarbonyl; aminocarbonyl wherein the amino group is optionally substituted by hydroxy, $(C_{1-6})$alkyl, hydroxy$(C_{1-6})$alkyl, aminocarbonyl$(C_{1-6})$alkyl, $(C_{2-6})$alkenyl, $(C_{1-6})$alkylsulphonyl, trifluoromethylsulphonyl, $(C_{2-6})$alkenylsulphonyl, $(C_{1-6})$alkoxycarbonyl, $(C_{1-6})$alkylcarbonyl, $(C_{2-6})$alkenyloxycarbonyl or $(C_{2-6})$alkenylcarbonyl and optionally further substituted by $(C_{1-6})$alkyl, hydroxy $(C_{1-6})$alkyl, aminocarbonyl$(C_{1-6})$alkyl or $(C_{2-6})$alkenyl; cyano; tetrazolyl; 2-oxo-oxazolidinyl optionally substituted by $R^{10}$; 3-hydroxy-3-cyclobutene-1,2-dione-4-yl; 2,4-thiazolidinedione-5-yl; tetrazol-5-ylaminocarbonyl; 1,2,4-triazol-5-yl optionally substituted by $R^{10}$; or 5-oxo-1,2,4-oxadiazol-3-yl; or $(C_{1-4})$alkyl or ethenyl optionally substituted with any of the substituents listed above for $R^3$ and/or up to 3 groups $R^{12}$ independently selected from:

thiol; halogen; $(C_{1-6})$alkylthio; trifluoromethyl; azido; $(C_{1-6})$alkoxycarbonyl; $(C_{1-6})$alkylcarbonyl; $(C_{2-6})$alkenyloxycarbonyl; $(C_{2-6})$alkenylcarbonyl; hydroxy optionally substituted by $(C_{1-6})$alkyl, $(C_{2-6})$alkenyl, $(C_{1-6})$alkoxycarbonyl, $(C_{1-6})$alkylcarbonyl, $(C_{2-6})$alkenyloxycarbonyl, $(C_{2-6})$alkenylcarbonyl or aminocarbonyl wherein the amino group is optionally substituted by $(C_{1-6})$alkyl, $(C_{2-6})$alkenyl, $(C_{1-6})$alkylcarbonyl or $(C_{2-6})$alkenylcarbonyl; amino optionally mono- or disubstituted by $(C_{1-6})$alkoxycarbonyl, $(C_{1-6})$alkylcarbonyl, $(C_{2-6})$alkenyloxycarbonyl, $(C_{2-6})$alkenylcarbonyl, $(C_{1-6})$alkyl, $(C_{2-6})$alkenyl, $(C_{1-6})$alkylsulphonyl, $(C_{2-6})$alkenylsulphonyl or aminocarbonyl wherein the amino group is optionally substituted by $(C_{1-6})$alkyl or $(C_{2-6})$alkenyl; aminocarbonyl wherein the amino group is optionally substituted by $(C_{1-6})$alkyl, hydroxy$(C_{1-6})$alkyl, aminocarbonyl$(C_{1-6})$alkyl, $(C_{2-6})$alkenyl, $(C_{1-6})$alkoxycarbonyl, $(C_{1-6})$alkylcarbonyl, $(C_{2-6})$alkenyloxycarbonyl or $(C_{2-6})$alkenylcarbonyl and optionally further substituted by $(C_{1-6})$alkyl, hydroxy$(C_{1-6})$alkyl, aminocarbonyl$(C_{1-6})$alkyl or $(C_{2-6})$alkenyl; oxo; $(C_{1-6})$alkylsulphonyl; $(C_{2-6})$alkenylsulphonyl; or $(C_{1-6})$aminosulphonyl wherein the amino group is optionally substituted by $(C_{1-6})$alkyl or $(C_{2-6})$alkenyl;

in addition when $R^3$ is disubstituted with a hydroxy or amino containing substituent and a carboxy containing substituent these may together form a cyclic ester or amide linkage, respectively; or when $R^3$ is in the 3-position $R^2$ and $R^3$ may together form a divalent residue $=CR^{5'}R^{6'}$ where $R^{5'}$ and $R^{6'}$ are independently selected from hydroen, $(C_{1-6})$alkyl, $(C_{2-6})$alkenyl, aryl$(C_{1-6})$alkyl and aryl$(C_{2-6})$alkenyl, any alkyl or alkenyl moiety being optionally substituted by up to three $R^{12}$ groups;

$R^4$ is $(C_{5-12})$alkyl, optionally substituted phenyl$(C_{2-3})$alkyl or optionally substituted phenyl$(C_{3-4})$alkenyl;

A is $CR^6R^7$ and B is $SO_2$, CO or $CH_2$ wherein:

each of $R^6$ and $R^7$ is independently selected from: hydrogen; $(C_{1-6})$alkoxy; thiol; $(C_{1-6})$alkylthio; halo; trifluoromethyl; azido; $(C_{1-6})$alkyl; $(C_{2-6})$alkenyl; $(C_{1-6})$alkoxycarbonyl; $(C_{1-6})$alkylcarbonyl; $(C_{2-6})$alkenyloxycarbonyl; $(C_{2-6})$alkenylcarbonyl; hydroxy, amino or aminocarbonyl optionally substituted as for corresponding substituents in $R^3$; $(C_{1-6})$alkylsulphonyl; $(C_{2-6})$alkenylsulphonyl; or $(C_{1-6})$aminosulphonyl wherein the amino group is optionally substituted by $(C_{1-6})$alkyl or $(C_{2-6})$alkenyl;

$R^{10}$ is selected from $(C_{1-4})$alkyl; $(C_{2-4})$alkenyl and aryl any of which may be optionally substituted by a group $R^{12}$ as defined above; carboxy; aminocarbonyl wherein the amino group is optionally substituted by hydroxy, $(C_{1-6})$alkyl, $(C_{2-6})$alkenyl, $(C_{1-6})$alkylsulphonyl, trifluoromethylsulphonyl, $(C_{2-6})$alkenylsulphonyl, $(C_{1-6})$alkoxycarbonyl, $(C_{1-6})$alkylcarbonyl, $(C_{2-6})$alkenyloxycarbonyl or $(C_{2-6})$alkenylcarbonyl and optionally further substituted by $(C_{1-6})$alkyl or $(C_{2-6})$alkenyl; $(C_{1-6})$alkylsulphonyl; trifluoromethylsulphonyl; $(C_{2-6})$alkenylsulphonyl; $(C_{1-6})$alkoxycarbonyl; $(C_{1-6})$alkylcarbonyl; $(C_{2-6})$alkenyloxycarbonyl and $(C_{2-6})$alkenylcarbonyl;

and $R^{11}$ is hydrogen; or $(C_{1-4})$alkyl or $(C_{2-4})$alkenyl optionally substituted with 1 to 3 groups selected from:

carboxy: $(C_{1-4})$alkoxycarbonyl; $(C_{1-4})$alkylcarbonyl; $(C_{2-4})$alkenyloxycarbonyl; $(C_{2-4})$alkenylcarbonyl; aminocarbonyl wherein the amino group is optionally substituted by hydroxy, $(C_{1-4})$alkyl, hydroxy$(C_{1-4})$alkyl, aminocarbonyl$(C_{1-4})$alkyl, $(C_{2-4})$alkenyl, $(C_{1-4})$alkylsulphonyl, trifluoromethylsulphonyl, $(C_{2-4})$alkenylsulphonyl, $(C_{1-4})$alkoxycarbonyl, $(C_{1-4})$alkylcarbonyl, $(C_{2-4})$alkenyloxycarbonyl or $(C_{2-4})$alkenylcarbonyl; cyano; tetrazolyl; 2-oxo-oxazolidinyl optionally substituted by $R^{10}$; 3-hydroxy-3-cyclobutene-1,2-dione-4-yl; 2,4-thiazolidinedione-5-yl; tetrazol-5-ylaminocarbonyl; 1,2,4-triazol-5-yl optionally substituted by $R^{10}$; 5-oxo-1,2,4-oxadiazol-3-yl; thiol; halogen; $(C_{1-4})$alkylthio; trifluoromethyl; azido; hydroxy optionally substituted by $(C_{1-4})$alkyl, ($C_{2-4}$)alkenyl, ($C_{1-4}$)alkoxycarbonyl, ($C_{1-4}$) alkylcarbonyl, ($C_{2-4}$)alkenyloxycarbonyl, ($C_{2-4}$) alkenylcarbonyl; oxo; ($C_{1-4}$)alkylsulphonyl; ($C_{2-4}$) alkenylsulphonyl; or ($C_{1-4}$)aminosulphonyl wherein the amino group is optionally substituted by ($C_{1-4}$)alkyl or ($C_{2-4}$)alkenyl.

2. A compound according to claim 1 wherein:
   (a) $Z^1$ is N, $Z^3$ is CH or CF, and $Z^2$, $Z^4$, and $Z^5$ are CH,
   (b) $Z^3$ is CH or CF and $Z^1$, $Z^2$, $Z^4$, and $Z^5$ are CH, or
   (c) $Z^5$ is N, $Z^3$ is CH or CF, and $Z^1$, $Z^2$, and $Z^4$ are CH.

3. A compound according to claim 1 or 2 wherein $R^1$ and $R^{1a}$ are independently methoxy, amino($C_{3-5}$)alkyloxy, guanidino($C_{3-5}$)alkyloxy, piperidyl($C_{3-5}$)alkyloxy, nitro or fluoro.

4. A compound according to claim 1 wherein $R^3$ is hydrogen; ($C_{1-4}$)alkyl; ethenyl; optionally substituted 1-hydroxy($C_{1-4}$)alkyl; carboxy; ($C_{1-6}$)alkoxycarbonyl; optionally substituted aminocarbonyl; carboxy($C_{1-4}$)alkyl; optionally substituted aminocarbonyl($C_{1-4}$)alkyl; cyano($C_{1-4}$)alkyl; optionally substituted 2-oxo-oxazolidinyl or optionally substituted 2-oxo-oxazolidinyl($C_{1-4}$alkyl).

5. A compound according to claim 1 wherein $R^3$ is in the 3-position and the substitutents at the 3- and 4-position of the piperidine ring are cis.

6. A compound according to claim 1 wherein A is CHOH or $CH_2$, and B is $CH_2$.

7. A compound according to claim 1 wherein $R^{11}$ is hydrogen.

8. A compound according to claim 1 selected from:
   1-Heptyl-4-[2-(R)-hydroxy-2-(6-methoxyquinolin-4-yl)] ethylaminopiperidine;
   cis-3-(R/S)-Ethoxycarbonyl-1-heptyl-4-(S/R)-[2-(R)-hydroxy-2-(6-methoxyquinolin-4-yl)] ethylaminopiperidine;
   cis-3-(R/S)-Aminocarbonyl-1-heptyl-4-(S/R)-[2-(R)-hydroxy-2-(6-methoxyquinolin-4-yl)] ethylaminopiperidine;
   cis-1-Heptyl-3-(R/S)-hydroxymethyl-4-(S/R)-[2-(R)-hydroxy-2-(6-methoxyquinolin-4-yl)] ethylaminopiperidine;
   cis-3-(R/S)-carboxy-1-heptyl-4-(S/R)-[2-(R)-hydroxy-2-(6-methoxyquinolin-4-yl)]ethylaminopiperidine;
   1-Heptyl-4-[2-(S)-hydroxy-2-(6-methoxyquinolin-4-yl)] ethylaminopiperidine; or
   1-Heptyl-4-[2-(R)-hydroxy-2-(6-methoxyquinolin-4-yl)] ethyl(N-methyl)aminopiperidine;
   or a pharmaceutically acceptable derivative thereof.

9. A pharmaceutical composition comprising a compound of formula (I) as defined in claim 1, or a pharmaceutically acceptable derivative thereof, and a pharmaceutically acceptable carrier.

10. A method of treatment of bacterial infections in mammals which method comprises the administration to a mammal in need of such treatment an effective amount of a compound of formula (I) as defined in claim 1, or a pharmaceutically acceptable derivative thereof.

11. A process for preparing a compound of formula (I) as defined in claim 1, or a pharmaceutically acceptable derivative thereof, which process comprises: reacting a compound of formula (IV) with a compound of formula (V):

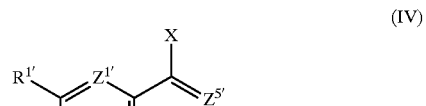

(IV)

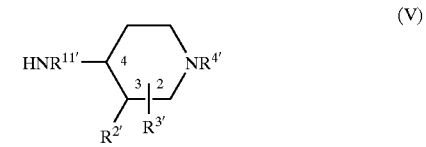

(V)

wherein $Z^{1'}$, $Z^{2'}$, $Z^{3'}$, $Z^{4'}$, $Z^{5'}$, $R^{11'}$, $R^{1'}$, $R^{2'}$, $R^{3'}$ and $R^{4'}$ are $Z^1$, $Z^2$, $Z^3$, $Z^4$, $Z^5$, $R^{11}$, $R^1$, $R^2$, $R^3$ and $R^4$ as defined in formula (I) or groups convertible thereto;

and:
(i) X is $CR^6R^7SO_2W$
(ii) X is A'-COW
(iii) X is $CR^6=CH_2$
(iv) X is oxirane and in which W is a leaving group e.g. halogen, A' is A as defined in formula (I), or a group convertible thereto, and oxirane is:

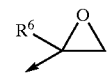

wherein $R^6$ and $R^7$ are as defined in formula (I);

and thereafter optionally or as necessary converting $Z^{1'}$, $Z^{2'}$, $Z^{3'}$, $Z^{4'}$, $Z^{5'}$, A', $R^{11'}$, $R^{1'}$, $R^{2'}$, $R^{3'}$ and $R^{4'}$ to $Z^1$, $Z^2$, $Z^3$, $Z^4$, $Z^5$, A, $R^{11}$, $R^1$, $R^2$, $R^3$ and $R^4$, converting A-B to other A-B, interconverting $R^{11}$, $R^1$, $R^2$, $R^3$ and/or $R^4$ and/or forming a pharmaceutically acceptable derivative thereof.

* * * * *